United States Patent [19]
Bidel et al.

[11] Patent Number: 5,849,786
[45] Date of Patent: Dec. 15, 1998

[54] PROCESS FOR THE TREATMENT OR PREVENTION OF HERPES

[76] Inventors: Christian-Georges Bidel, 77 résidence Camarat Boulevard Leader — 06400, Cannes; Jean Poirson, 2 impasse des Glycines — Le Clos de Mougins — 06250, Mougins, both of France

[21] Appl. No.: 632,420
[22] PCT Filed: Oct. 7, 1994
[86] PCT No.: PCT/FR94/01176
§ 371 Date: Apr. 24, 1996
§ 102(e) Date: Apr. 24, 1996
[87] PCT Pub. No.: WO95/09635
PCT Pub. Date: Apr. 13, 1995

[30] Foreign Application Priority Data

Oct. 7, 1993 [FR] France ................................. 93 11951

[51] Int. Cl.$^6$ .................................................. A61K 31/355
[52] U.S. Cl. ............................................................. 514/458
[58] Field of Search ............................................. 514/458

[56] References Cited

PUBLICATIONS

Wilkinson 117CA: 205185U 1992.
Konoshima et al. 111 CA 224819 X 1989.

*Primary Examiner*—Marianne M. Cintins
*Attorney, Agent, or Firm*—Oblon, Spivak, McClelland, Maier & Neustadt, P.C.

[57] ABSTRACT

The present invention related to the use of at least one active ingredient of the flavonoid family in the preparation of compositions for the treatment and/or prevention of herpes.

10 Claims, No Drawings

PROCESS FOR THE TREATMENT OR PREVENTION OF HERPES

This application is a 371 of PCT/FR94/01176 filed Oct. 7, 1998.

BACKGROUND OF THE INVENTION

1. The Field of the Invention

The present invention relates to the preparation of new compositions intended for the prevention and/or treatment of herpes outbreaks.

2. Discussion of the Background

Herpes is an extremely contagious disease caused by a type 1 or 2 Herpes simplex virus, the sole reservoir of which is man.

It can attack the skin or mucous membranes and is spread by simple contact, increasing in proportion the number of individuals exposed to the risks related to this disease. Herpetic primary phase is especially observed in children, where it appears as very painful, pruriginous vesicular lesions which often burst and which often attack the mouth and tongue.

In addition to being a nuisance (pain, stress, appearance), herpes is a disease which can have serious consequences, in particular for people in poor health, pregnant women or neonates, and in cases of eye complaints.

There currently exists no effective treatment against this viral disease. Certain therapies can bring relief during eruptions and can possibly reduce the duration thereof but do not prevent their development. This is the case with the most widely used of them: acyclovir marketed by Wellcome Laboratories under the name Zovirax®.

Flavonoids are polyphenols which contain a skeleton based on 15 carbon atoms resulting from the fusion of two aromatic units, one of which derives from benzene and the other from phenylpropane. The most widespread are the anthocyanins, flavones and flavonols which can exist either in the free form or bonded to one or more sugars (heterosides).

Bioflavonoids or citroflavonoids or vitamin P complex have been known first of all for their favourable activity on blood vessels, by decreasing capillary permeability and fragility, and their synergic activity with ascorbic acid. They derive from flavones, of general formula I:

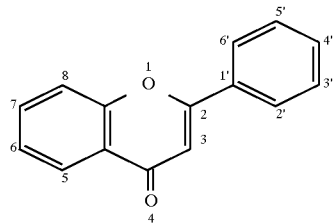

I

Semisynthetic flavone derivatives have been prepared, for example, in Applications EP 290,915 or EP 319,412. Different groups of flavone derivatives have been used for pharmaceutical applications other than those initially described.

EP 505,937 describes the preparation of flavone derivatives containing carbamoyl and sulfate groups and their use for their anti-elastase properties.

Flavone derivatives have been proposed for their activity in the treatment of cystinic lithiasis, as an anti-neoplastic or smooth muscle relaxant or in the treatment of diabetes.

EP 183,169 relates to halohydroxyflavones and to their use in medicaments for the treatment of hyperthyroidism.

In Application EP 450,588, derivatives of 3-oxoalkylflavone type are prepared and their hypocholesterolemic action is reported.

Antiviral compositions containing a combination of an antiviral agent and a glycoside which can derive from flavones make it possible to decrease the side effects commonly observed and are described in EP 312,222.

Application EP 19,081 was filed for new substituted flavone derivatives, used for the preparation of medicaments intended to combat Rhinoviruses and Enteroviruses.

Phosphorylated flavonoid derivatives are proposed in EP 543,555 for their activity, in particular against HIV.

SUMMARY OF THE INVENTION

The Applicant has surprisingly revealed the preventive and/or curative activity against herpes outbreaks of compositions containing non-phosphorylated flavonoids, and more particularly citroflavonoids.

The subject of the present invention is therefore the use of at least one active principle from the flavonoid family for the preparation of compositions intended for the treatment and/or the prevention of herpes.

DETAILED DESCRIPTION OF THE PREFERRED EMBODIMENTS

The flavonoids are natural flavonoids and more particularly citroflavonoids and semisynthetic flavone derivatives.

Flavonoid heterosides are advantageously used for the preparation of the compositions. The flavonosides contain one or more saccharide units, which can especially be rutinose, mannose, glucose, and the like.

The useful flavonoids according to the invention are preferably substituted in the 4'-position by a methoxy radical.

In fact, effectiveness in the prevention and/or treatment of herpes attacks is observed for compositions which contain diosmin or hesperidin. Advantageous results are also obtained with compositions which contain a combination of diosmin and hesperidin, which suggests the existence of a synergy of the activities of these two compounds.

On the other hand, compositions which contain rutin have no effect in the applications according to the invention; the rutin molecule is substituted by a hydroxyl in the 4'-position.

Diosmin and/or hesperidin have been administered in man for several years in other indications. They are compounds which are well tolerated, causing few side effects, and whose pharmaceutical formulation is well understood. At the doses commonly used to protect blood vessels, these compounds are active for the treatment and/or prophylaxis of herpes attacks. In particular, the compositions according to the invention can be formulated in the form of unit doses containing from 100 to 900 mg of diosmin.

According to one of the aspects of the invention, flavonoids are used in the preparation of pharmaceutical compositions intended for the prevention and/or treatment of herpes outbreaks.

According to another aspect, the compositions according to the invention are for cosmetic and/or dermocosmetic use.

The compositions prepared according to the invention make it possible to prevent the development of type 1 or 2 herpes attacks.

They greatly reduce the effects thereof, in particular the very significant infectiousness during the secondary phase during which the herpetic cluster bursts out, the serious consequences such as those resulting from eye complaints and on the comfort of the sufferers.

The Applicant has shown that certain flavonoids, alone or in combination, are very effective for the treatment of herpes and that, at various stages of the development of the disease:

a preventive use prevents any appearance of herpes, an early curative use makes it possible to halt an attack during development, a late curative use makes it possibly to shorten healing times and to prevent painful effects.

The compositions additionally contain pharmaceutically and/or cosmetologically acceptable vehicles and excipients known to those skilled in the art.

The compositions prepared according to the invention can contain excipients suited to a formulation for oral administration, such as drops, tablets and gelatin capsules. The composition is advantageously formulated as a unit dose containing from 20 mg to 800 mg of hesperidin.

The compositions according to the invention can be in a form suited to local administration, for example in the form of a cream, ointment, lotion, eyewash or solid stick.

The flavonoids, in the uses according to the invention, can be combined with other active principles capable of reinforcing their action.

The examples which follow are intended to illustrate the invention without limiting the scope thereof in any way.

EXAMPLE 1

A man aged 43 years, suffering for a number of years from chronic genital herpes with outbreaks at approximately monthly intervals, did not record any attack for a period of 5 months during which he absorbed orally 3 times daily 450 mg of diosmin and 50 mg of hesperidin in the form of sugar-coated tablets (Daflon® 500 marketed by Laboratoires Servier). The herpes attacks reappeared when the treatment was halted.

EXAMPLE 2

The absorption by the subject mentioned in Example 1, from the first signs of the herpes outbreak (tingling, sensation of burning), 5 times orally of 900 mg of diosmin and 100 mg of hesperidin (2 sugar-coated tablets of Daflon® 500) distributed over a period of 36 hours completely halted the attack, without the appearance of the usual lesions (herpetic cluster). This result was verified continually for a period of 14 months.

EXAMPLE 3

The substitution in Example 2 of 900 mg of diosmin and 100 mg of hesperidin by 300 mg of diosmin and 300 mg of hesperidin (2 sugar-coated tablets of Daflon® 375 in place of Daflon® 500) produced the same result, namely halting the development of a nascent herpes outbreak.

EXAMPLE 4

The substitution in Example 2 of 900 mg of diosmin and 100 mg of hesperidin by 450 mg of diosmin and 50 mg of hesperidin (1 sugar-coated tablet of Daflon® 500 in place of 2) did not make it possible to produce the same result, the herpes outbreak having developed towards the appearance of vesicles and then lesions, although less virulently than when no treatment was used. This result having been confirmed on a number of occasions, it would seem, on comparing these treatment conditions with those of Example 3, that the combination of diosmin and hesperidin has a synergic nature in the treatment of herpes attacks.

EXAMPLE 5

The substitution in Example 2 of 900 mg of diosmin and 100 mg of hesperidin by 600 mg of hesperidin (Hesperidin 97%, reference 29, 260-5 of Aldrich-Chimie Sarl) as an aqueous dispersion produced the same result, namely halting the development of a nascent herpes outbreak.

EXAMPLE 6

Example 4 was repeated a number of times, the oral treatment being complemented by a local treatment with an ointment containing 5% hesperidin (Hesperidin 97%, reference 29, 260-5 from Aldrich-Chimie Sarl) dispersed in a hydrophilic base (Biobase from Laboratoires Bioderma). The outbreak ceased to develop after 24 hours and was reabsorbed during the following 48 hours.

EXAMPLE 7

A man aged 45 years had suffered for many years from herpes labialis with outbreaks at approximately monthly intervals. The absorption by this subject, from the first signs of the herpes outbreak, 5 times orally of 900 mg of diosmin and 100 mg of hesperidin (2 sugar-coated tablets of Daflon® 500) distributed over a period of 36 hours completely halted the attack, with rapid resorption of the nascent vesicle and without appearance of the usual lesions. This result was verified continually over a period of 14 months.

EXAMPLE 8

The substitution in Example 5 of 900 mg of diosmin and 100 mg of hesperidin by 600 mg of hesperidin (Hesperidin 97%, reference 29, 260-5 from Aldrich-Chimie Sarl) as an aqueous dispersion produced the same result, namely halting the development of a nascent herpes outbreak.

EXAMPLE 9

A woman aged 47 years had suffered for many years from lumber herpes with outbreaks at approximately monthly intervals. The absorption by this subject, from the first signs of the herpes outbreak, 5 times orally of 900 mg of diosmin and 100 mg of hesperidin (2 sugar-coated tablets of Daflon® 500) distributed over a period of 36 hours, completely halted the attack, with rapid resorption of the nascent vesicles and without appearance of the usual lesions. This result was verified continually over a period of 14 months.

EXAMPLE 10

A woman aged 40 years, subject to herpes attacks in the right eye, was no longer subject to this complaint, with its potentially serious consequences, by absorbing, on the first signs of burning, 5 times orally 900 mg of diosmin and 100 mg of hesperidin (2 sugar-coated tablets of Daflon® 500) distributed over a period of 36 hours. This result was verified continually over a period of 26 months.

We claim:

1. A method for treating or preventing herpes, comprising administering to a patient in need thereof an anti-herpes treatment, the active component of which consists of a flavonoid heteroside selected from the group consisting of hesperidin, diosmin and combinations thereof.

2. The method of claim 1, wherein said flavonoid heteroside is administered orally.

3. The method of claim 2, wherein said flavonoid heteroside is admixed and administered in unit dosage form.

4. The method of claim 2, wherein said flavonoid heteroside is hesperidin, the latter being admixed and administered in unit dose form comprising from 20–800 mg of hesperidin.

5. The method of claim 2, wherein said flavonoid heteroside is hesperidin the latter being administered in the form of an aqueous dispersion.

6. The method of claim 1, wherein said flavonoid heteroside is administered topically.

7. The method of claim 6, wherein said flavonoid heteroside is hesperidin in the form of a composition consisting of 5% hesperidin dispersed in a hydrophilic base.

8. The method of claim 1, wherein said flavonoid heteroside is in the form of a dermocosmetic composition.

9. The method of claim 1, wherein said flavonoid heteroside is in the form of a pharmaceutical composition.

10. The method of claim 1, wherein said flavonoid heteroside is in the form of a cream, ointment, lotion, eye wash or solid stick.

* * * * *

UNITED STATES PATENT AND TRADEMARK OFFICE
CERTIFICATE OF CORRECTION

PATENT NO. : 5,849,786

DATED : DECEMBER 15, 1998

INVENTOR(S): CHRISTIAN-GEORGES BIDEL ET AL

It is certified that an error appears in the above-identified patent and that said Letters Patent is hereby corrected as shown below:

Column 1, lines 4-5, "Oct. 7, 1998." should read --Oct. 7, 1994.--.

Signed and Sealed this

Fourteenth Day of September, 1999

*Attest:*

Q. TODD DICKINSON

*Attesting Officer*   *Acting Commissioner of Patents and Trademarks*